United States Patent [19]
Levin

[11] Patent Number: 6,015,793
[45] Date of Patent: Jan. 18, 2000

[54] USE OF TAGATOSE TO ENHANCE KEY BLOOD FACTORS

[75] Inventor: Gilbert V. Levin, Annapolis, Md.

[73] Assignee: Biospherics Incorporated, Beltsville, Md.

[21] Appl. No.: 09/299,023

[22] Filed: Apr. 26, 1999

[51] Int. Cl.$^7$ .................................................. A61K 31/70
[52] U.S. Cl. .............................................. 514/23; 514/25
[58] Field of Search ......................................... 514/23, 25

[56] References Cited

U.S. PATENT DOCUMENTS

| | | | |
|---|---|---|---|
| 4,786,722 | 11/1988 | Zehner | 536/1.1 |
| 5,002,612 | 3/1991 | Beadle et al. | 127/46.1 |
| 5,078,796 | 1/1992 | Beadle et al. | 127/46.1 |
| 5,356,879 | 10/1994 | Zehner et al. | 514/25 |

*Primary Examiner*—Phyllis G. Spivack
*Attorney, Agent, or Firm*—Roylance, Abrams, Berdo & Goodman, L.L.P.

[57] ABSTRACT

A method for enhancing the blood factors of a mammal comprising administering to a mammal in need of such enhancement an efficacious amount of tagatose.

9 Claims, No Drawings

USE OF TAGATOSE TO ENHANCE KEY BLOOD FACTORS

BACKGROUND OF THE INVENTION

This invention relates to the use of tagatose to improve one or more specific blood factors in persons suffering from, or having propensities toward, diseases associated with abnormalities in key blood factors.

A variety of diseases is caused by or results in abnormalities in key blood factors. These factors include red blood cell count (RBC), prothromin time (PT), activated partial thromboplastin time (APTT), and fibrinogen (FIB).

In 13-week studies performed with normal rats, four test groups were placed on normal diets in which 5, 10, 15 or 20 percent by weight, respectively, was replaced with tagatose. Two control groups were included, one maintained on normal diet with no replacement; the other on normal diet in which 20 percent by weight was replaced with cellulose and fructose at 10 percent each.

At the end of the study, all animals were sacrificed and hematological analyses performed on each. The results of these analyses are shown in Table 1. The table demonstrates that the inclusion of tagatose in the diet proved advantageous for each of the above parameters. The RBC and FIB factors for those animals fed tagatose were each increased over the corresponding measurements in the control animals. The increased values were within, or near, the normal range. The PT and APTT values decreased over the study period, staying within the normal range.

Specifically, increases in RBC indicate improved hematopoiesis and better maintenance of the blood and its functions. The decreases in PT and APTT, and the increase in FIB are measures of quicker and better clotting of the blood.

The food additive and new drug regulations of the U.S. FDA endorse the use of rats as good models for the human systems in safety and efficacy studies.

TABLE 1

| | Hematological Values | | | |
|---|---|---|---|---|
| | RBC, $\times 10^6$ | PT,s | APTT,s | FIB mg/dl |
| 0% Control | | | | |
| Male | 7.98 ± 0.29 | 10.9 ± 1.1 | 18.7 ± 2.2 | 260.7 ± 40.0 |
| Female | 7.38 ± 0.31 | 9.8 ± 0.6 | 15.1 ± 1.9 | 228.4 ± 77.1 |
| Cellulose/fructose control | | | | |
| Male | 8.10 ± 0.27 | 11.9 ± 1.6 | 19.9 ± 3.1 | 249.9 ± 37.3 |
| Female | 7.49 ± 0.34 | 9.8 ± 0.4 | 14.4 ± 1.8 | 187.9 ± 46.2 |
| 5% D-tagatose | | | | |
| Male | 8.02 ± 0.28 | 11.3 ± 1.2 | 19.5 ± 1.7 | 254.5 ± 45.2 |
| Female | 7.41 ± 0.24 | 10.1 ± 0.4[c] | 15.6 ± 1.7[c] | 216.0 ± 115.8 |
| 10% D-tagatose | | | | |
| Male | 8.03 ± 0.23 | 11.1 ± 0.9 | 18.9 ± 2.0 | 275.3 ± 66.2 |
| Female | 7.29 ± 0.70 | 9.6 ± 0.8 | 14.3 ± 1.4 | 229.9 ± 82.0 |
| 15% D-tagatose | | | | |
| Male | 8.09 ± 0.44 | 10.7 ± 0.9[c] | 18.7 ± 3.0 | 319.4 ± 113.3[a,d] |
| Female | 7.48 ± 0.27 | 9.8 ± 0.7 | 13.7 ± 1.1[c] | 236.0 ± 52.9[c] |
| 20% D-tagatose | | | | |
| Male | 8.29 ± 0.36[a] | 10.7 ± 0.9[c] | 18.6 ± 2.4 | 290.3 ± 49.0[c] |
| Female | 7.51 ± 0.37 | 9.5 ± 0.7 | 13.4 ± 1.3[b] | 261.4 ± 50.3[a,d] |

Note.
Values are means ±SD (n = 18–20 rats). Hematology abbreviations are defined in the text. Unit abbreviations; g/dl (grams/deciliter), mg/dl (milligrams/deciliter), fl (femtoliter), pg (picogram), s (seconds).
Levels of statistical significance indicated by superscript letters.
[a]Mean significantly different than 0% control ($P \leq 0.05$).
[b]Mean significantly different than 0% control ($P \leq 0.01$).
[c]Mean significantly different than cellulose/fructose control ($P \leq 0.05$).
[d]Mean significantly different than cellulose/fructose control ($P \leq 0.01$).

SUMMARY OF THE INVENTION

In accordance with this invention, there is provided a method for enhancing key blood factors of a mammal, especially man, in need of such treatment which comprises administering to said mammal an efficacious amount of tagatose, i.e., D-tagatose, L-tagatose or a mixture of the two isomers.

DETAILED DESCRIPTION OF THE INVENTION

The tagatose may be administered to a subject in combination with a food, beverage or taken separately in powder, crystalline or liquid form. As diluent, if needed, one may use liquid or solid carriers such as water, starch, alcohol or other non-toxic substances. Preferably, the tagatose is administered in the weight range of 100 mg/kg body weight/day to 2000 mg/kg body weight/day. The tagatose may be administered daily, every other day or at other prescribed frequencies. It may be administered in combination with other medications known to be suitable for use in the treatment of the particular blood disorder being treated.

EXAMPLE 1

Treatment of Anemia

A human subject is diagnosed as anemic by virtue of reduced RBC levels, and confirmed by other analyses showing blood iron deficiency and the presence of excessive microcells. The patient is placed on a regimen of tagatose taken at a prescribed rate, for example, 30 g/day divided into 10 g doses at each meal for a prescribed period of time. The RBC level is monitored periodically. Within several weeks, improvement in the RBC level is shown. Upon continuing the treatment, the RBC level becomes normal. At the discretion of the patient's physician, the tagatose treatment is continued, modified or discontinued, to be re-started in event of a relapse.

EXAMPLE 2

Adjunct Treatment of Hemophilia

A human patient is diagnosed with hemophilia. The patient's PT and APTT are at dangerous levels, indicating slow clotting time. The patient's FIB level is low, also indicating dangerously slower clotting time. Should bleeding from injury or disease take place, death could result before clotting stopped the bleeding. The patient is placed on a regimen of tagatose taken at a prescribed rate, for example, 15 g/day divided into 5 g doses at each meal, and the patient's progress is followed. Within several weeks, analyses show that the PT and APTT levels have decreased and the FIB level has begun to increase. Continued treatment with tagatose, with or without other prescribed treatments, brings the PT, APTT, and FIB levels near or within normal ranges. At the discretion of the patient's physician, the tagatose treatment is continued, modified or discontinued.

What is claimed is:

1. A method for treating anemia or hemophilia in a mammal comprising administering to a mammal in need of such treatment an efficacious amount of tagatose.

2. The method of claim 1 wherein the mammal is a human.

3. The method of claim 1 wherein from 100–2000 mg/kg body weight/day is administered to said mammal.

4. The method of claim 1 wherein the prescribed dose is taken every day.

5. The method of claim 1 wherein the prescribed dose is taken every other day.

6. The method of claim 1 wherein said tagatose is used in combination with a medication known to be useful in the treatment of the blood disorder being treated.

7. The method of claim 1 wherein said mammal is being treated for anemia.

8. The method of claim 1 wherein said mammal is being treated for hemophilia.

9. The method of claim 1 wherein the tagatose is D-tagatose, L-tagatose or a mixture of the two isomers.

* * * * *